United States Patent
Majeed et al.

(10) Patent No.: US 8,193,156 B1
(45) Date of Patent: Jun. 5, 2012

(54) DIPEPTIDES INCORPORATING SELENOAMINO ACIDS WITH ENHANCED BIOAVAILABILITY—SYNTHESIS, PHARMACEUTICAL AND COSMECEUTICAL APPLICATIONS THEREOF

(75) Inventors: Muhammed Majeed, East Windsor, NJ (US); Kalyanam Nagabhushanam, East Windsor, NJ (US); Rajendran Ramanujam, Bangalore (IN); Renukeshwar H Chandramouli, Bangalore (IN)

(73) Assignee: Sami Labs Ltd, Bangalore ( * ) Notice: Subject to any disclaimer, the term of this patent is extended or adjusted under 35 U.S.C. 154(b) by 0 days.

(21) Appl. No.: 13/175,016

(22) Filed: Jul. 1, 2011

Related U.S. Application Data

(63) Continuation of application No. 11/749,184, filed on May 16, 2007, now Pat. No. 8,003,614.

(60) Provisional application No. 60/767,528, filed on May 18, 2006.

(51) Int. Cl.
*A61K 38/05* (2006.01)

(52) U.S. Cl. .................... 514/21.91; 514/7.6; 514/20.7; 514/706

(58) Field of Classification Search ............... 514/21.91, 514/7.6, 20.7, 706
See application file for complete search history.

(56) References Cited

OTHER PUBLICATIONS

Bloc, J. Agric. Food Chem. 49, 458-470, 2001.*

* cited by examiner

*Primary Examiner* — David Lukton

(57) ABSTRACT

Disclosed is a novel synthetic method for isomeric peptides through an appropriate linkage of L-selenomethionine or Se-Methyl-L-selenocysteine with L-glutamic acid. The novel synthetic method produces isomeric peptides of L-selenomethionine or Se-Methyl-L-selenocysteine that exhibit (i) enhanced water solubility; (ii) enhanced rate of dissolution in water; (iii) enhanced bioavailability; (iv) excellent vascular endothelial growth factor promoting activity; (v) excellent anti-5-alpha-reductase activity; (vi) capabilities to prevent/reduce "hair fall" and promote "hair growth", thereby maintaining a perfect homeostasis for "hair care". Cosmeceutical and pharmaceutical compositions comprising the isomeric peptides obtained through an appropriate linkage of L-selenomethionine or Se-Methyl-L-selenocysteine with L-glutamic acid are also disclosed. Other dipeptides with several other amino acids and uses thereof are also disclosed.

3 Claims, 8 Drawing Sheets

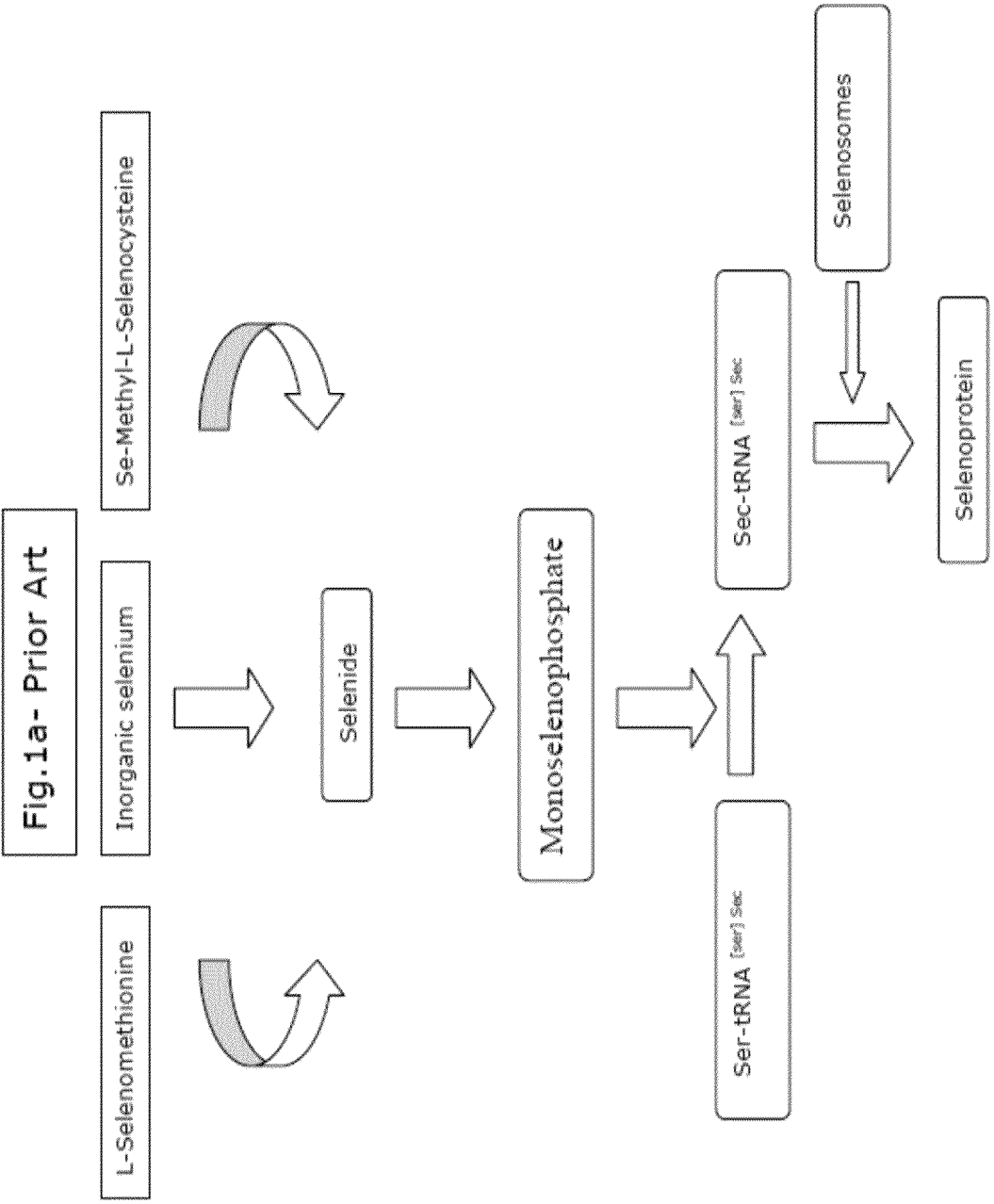

Fig 1b: PMR of γ-(N-Phthaloyl-L-glutamyl)-Se-methyl-L-selenocysteine
RR3_043 DMSO Solvent 400MHz
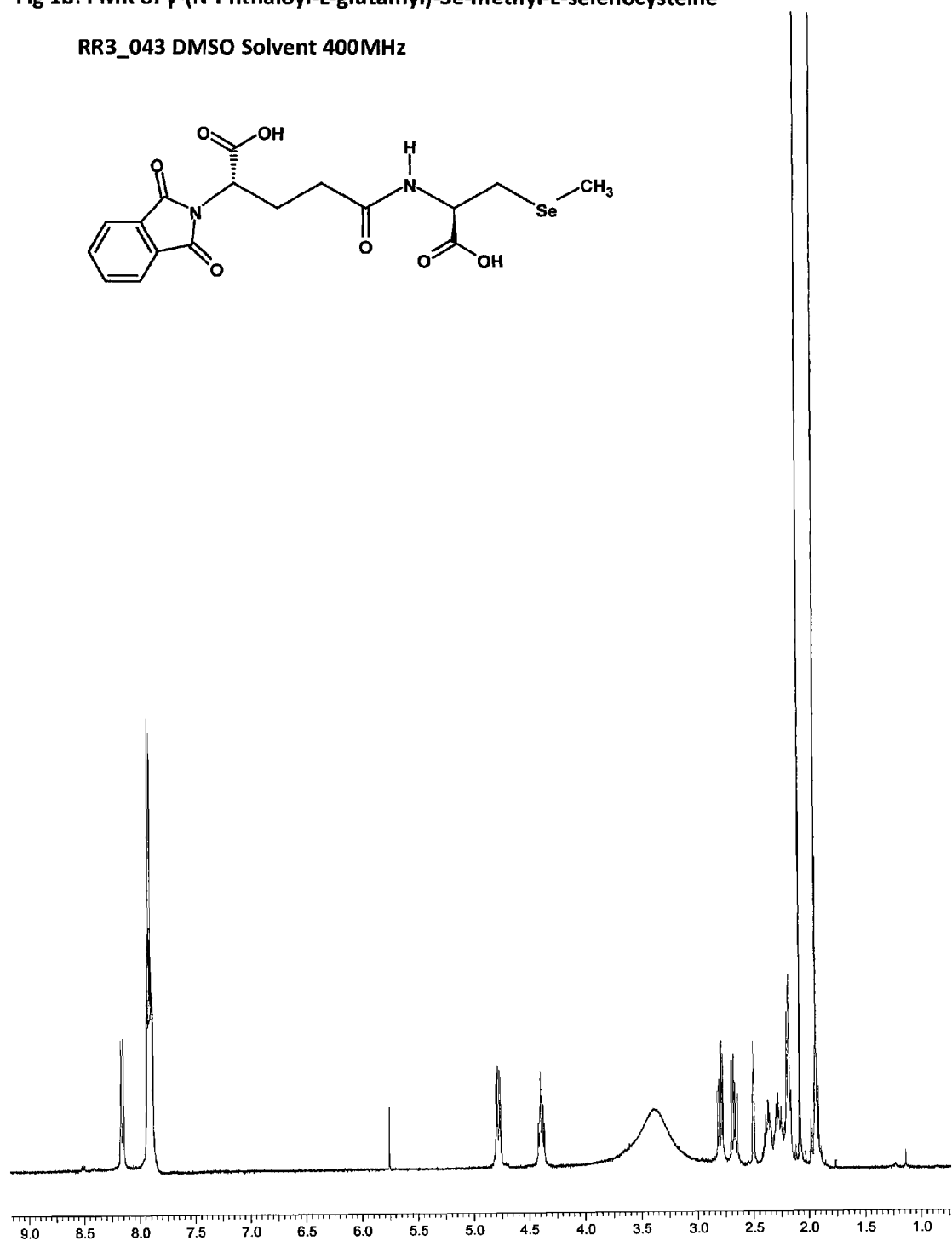

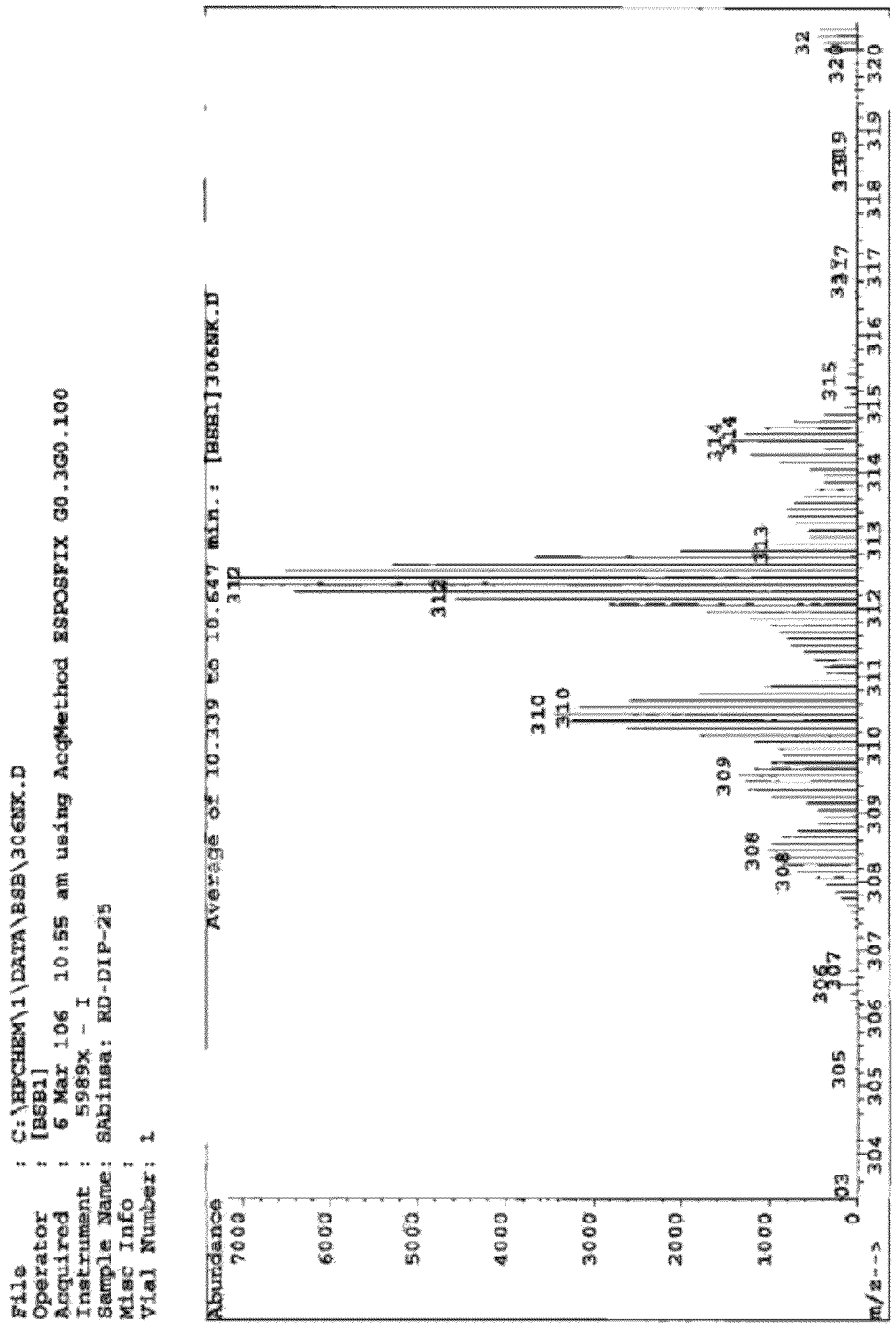
Fig 2: Mass Spectra of γ-L-glutamyl-Se-methyl-L-selenocysteine

Fig 3: PMR of γ-L-Glutamyl-Se-methyl-L-selenocysteine
RR3-048A D2O Solvent 500 MHz
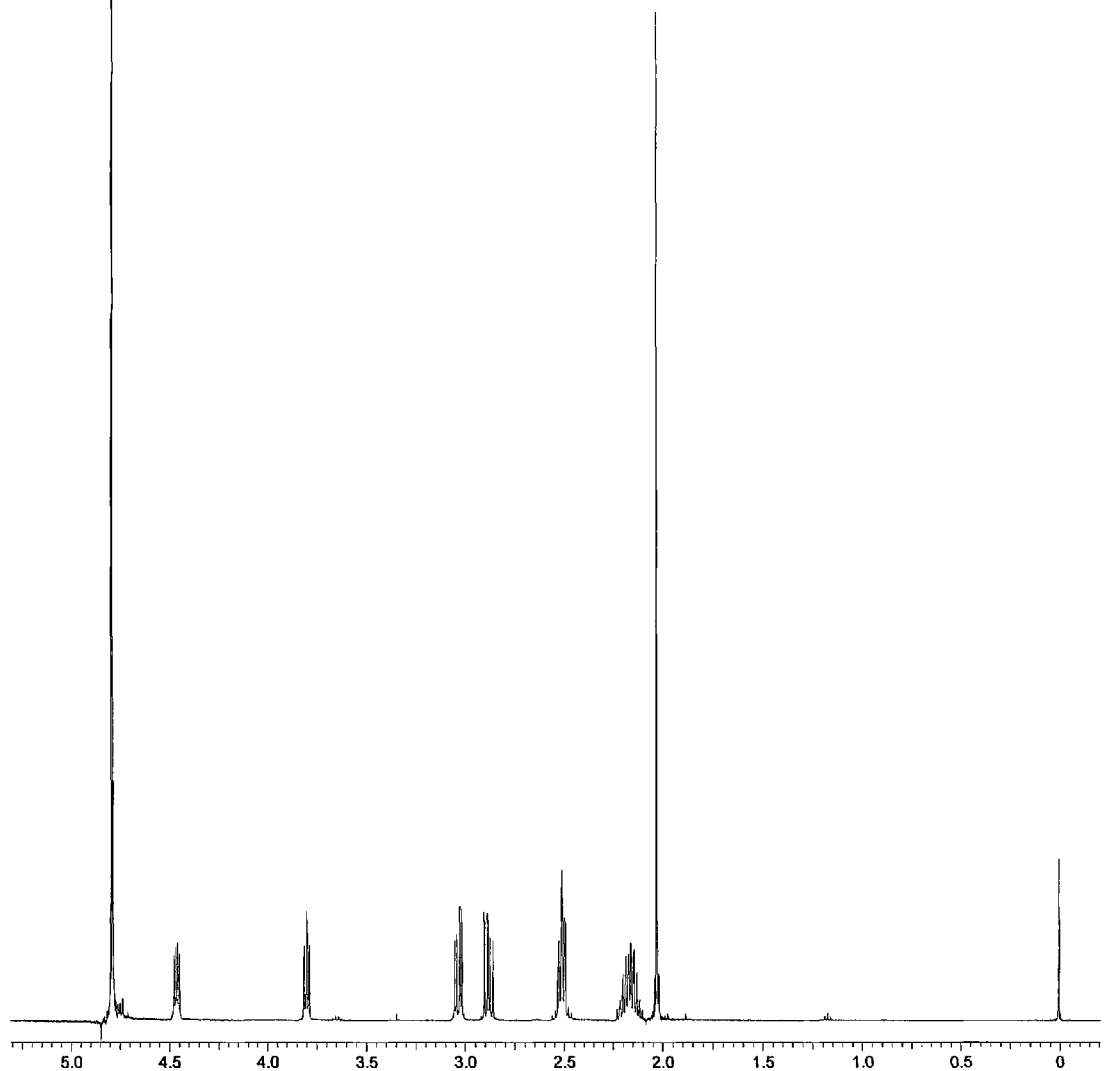

Fig 4: PMR of γ-L-Glutamyl-L-selenomethionine
RR4_139 (Rec.) D2O Solvent 300 MHz
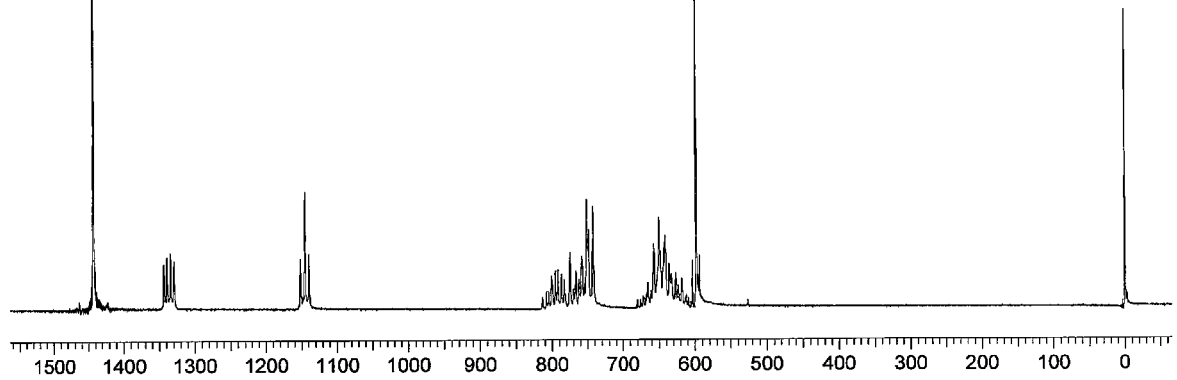

Fig 5: Single Crystal X-ray Structure of γ-L-Glutamyl-L-selenomethionine
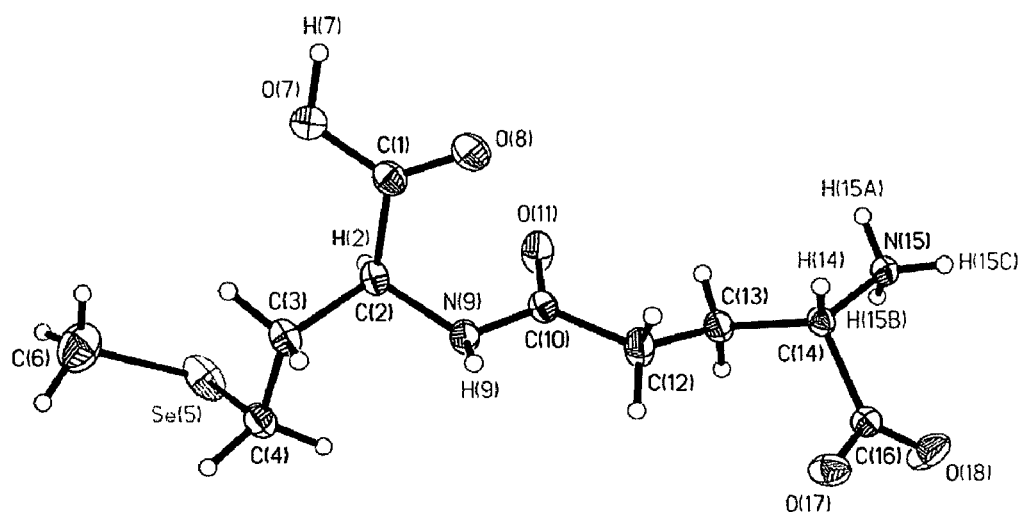

DIPEPTIDES INCORPORATING SELENOAMINO ACIDS WITH ENHANCED BIOAVAILABILITY—SYNTHESIS, PHARMACEUTICAL AND COSMECEUTICAL APPLICATIONS THEREOF

This application is a continuation of U.S. non-provisional application Ser. No. 11/749,184 filed on May 16, 2007 now U.S. Pat. No. 8,003,614, which claims the benefit of provisional application 60/767,528 filed on May 18, 2006 the disclosure of which is hereby incorporated for reference.

FIELD OF THE INVENTION

The invention relates to synthetic selenopeptides in general. More specifically, the invention relates to a novel synthetic method for the isomeric peptides through an appropriate linkage of L-selenomethionine or Se-Methyl-L-selenocysteine with L-glutamic acid which results in (i) enhanced water solubility of the isomeric peptides; (ii) enhanced rate of dissolution of the isomeric peptides in water; (iii) enhanced bioavailability of the isomeric peptides; (iv) isomeric peptides with excellent vascular endothelial growth factor promoting activity; (v) isomeric peptides with excellent anti-5-alpha-reductase activity; (vi) isomeric peptides that prevent "hair fall" and promote "hair growth" thereby maintaining a perfect homeostasis for "hair care".

BACKGROUND OF THE INVENTION

Most trace elements function through proteins of which they are constituents. Selenium is incorporated as the amino acid selenocysteine during translation of primary protein structure. Selenocysteine is synthesized and inserted into proteins co-translationally by a complex process.

Regardless of the form in which the selenium is ingested, it is transformed by a variety of metabolic pathways via the same intermediary pool into the specific selenocysteine-containing selenoproteins which are responsible for the biological effects of selenium. The levels of selenocysteine-containing selenoproteins in tissues appear to be controlled by homeostatic means. The common sources of selenium in animal nutrition including selenomethionine, Se-methyl-selenocysteine, selenite and selenate take different pathways to the intermediary selenium pool which is ultimately incorporated in the specific seleno-proteins or further converted into polar metabolites that can be readily excreted. An overview of selenoprotein biosynthesis is illustrated as FIG. 1.

The steps of seleno protein biosynthesis include (i) Dietary and tissue forms of selenium are converted to selenide; (ii) The enzyme selenophosphate synthetase acts upon the selenide or its closely related form (substrate) to form monoselenophosphate as a product. (iii) Monoselenophosphate is utilized to transform ser-tRNA$^{[ser]Sec}$ to selenocysteine. The selenocysteyl-tRNA$^{[ser]Sec}$ is inserted into the growing polypeptide chain of the selenoprotein by a selenosome complex.

Families of selenoproteins include the glutathione peroxidases, the iodothyronine deiodinases and the thioredoxin reductases. These are redox enzymes that take advantage of the chemical properties of selenium to catalyze, respectively, removal of hydroperoxides by glutathione, deiodination of thyroid hormones and support of cellular processes requiring reduction of disulfides. Several additional selenoproteins have been identified.

An insight into animal selenoproteins in relation to their biological functions is illustrated in the following table.

| Selenoprotein | Known Function |
|---|---|
| Glutathione peroxidases | *Hydroperoxide Catabolism* [Arthur, J. R. (2000) The glutathione peroxidases. Cell. Mol. Life Sci. 57: 1825-1835.] *Sperm structure* [Ursini, F., Heim, S., Kiess, M., Maiorino, M., Roveri, A., Wissing, J. & Flohe´, L. (1999) Dual function of the selenoprotein PHGPx during sperm maturation. Science 285: 1393-1396.] [Pfeifer H., Conrad M., Roethein D., Kyriakopoulos A., Brielmeier M., Bornkamm G. W., Behne D. Identification of a Specific Sperm Nuclei Selenoenzyme Necessary for Protamine Thiol Cross-Linking During Sperm Maturation. FASEB J 15: 1236-1238 (2001)] |
| Thioredoxin reductases | *Protein thiol redox regulation* [Arne´r, E. S. J. & Holmgren, A. (2000) Physiological functions of thioredoxin and thioredoxin reductase. Eur. J. Biochem. 267: 6102-6109.] *Vitamin C recycling* [May, J. M., Mendiratta, S., Hill, K. E. & Burk, R. F. (1997) Reduction of dehydroascorbate to ascorbate by the selenoenzyme thioredoxin reductase. J. Biol. Chem. 272: 22607-22610.] *Synthesis of DNA* [Arne´r, E. S. J. & Holmgren, A. (2000) Physiological functions of thioredoxin and thioredoxin reductase. Eur. J. Biochem. 267: 6102-6109.] |
| Iodothyronine deiodinases | $T_4$*activation, $T_3$inactivation* [Bianco, A. C., Salvatore, D., Gereben, B., Berry, M. J. & Larsen, P. R. (2002) Biochemistry, cellular and molecular biology, and physiological roles of the iodothyronine selenodeiodinases. Endocr. Rev. 23: 38-89. |
| Methionine sulfoxide Reductase B | *Removal of reactive oxygen species through methionine* [Moskovitz, J., Singh, V. K., Requena, J., Wilkinson, B. J., Jayaswal, R. K. & Stadtman, E. R. (2002) Purification and characterization of methionine sulfoxide reductases from mouse and *Staphylococcus aureus* and their substrate stereo specificity. Biochem. Biophys. Res. Commun. 290: 62-65. |
| Selenoprotein W | *Antioxidant* [Sun, Y., Gu, Q. P. & Whanger, P. D. (2001) Selenoprotein W in over expressed and under-expressed rat glial cells in culture. J. Inorg. Biochem. 84: 151-156.] |
| Selenoprotein P | *Selenium transport* [Burk, R. F., Hill, K. E., Read, R. & Bellew, T. (1991) Response of rat selenoprotein P to selenium administration and fate of its selenium. Am. J. Physiol. 261: E26-E30.] Hill, K. E., Zhou, J. D., McMahan, W. J., Motley, A. K., Atkins, J., Gesteland, R. & Burk, R. F. (2002) Characterization of selenoprotein P knockout mice. FASEB J. 16: A605. *Antioxidant* [Burk, R. F., Hill, K. E., Awad, J. A., Morrow, J. D., Kato, T., Cockell, K. A. & Lyons, P. R. (1995) Pathogenesis of diquat-induced liver necrosis in selenium deficient rats. Assessment of the roles of lipid peroxidation by measurement of F2 isoprostanes. Hepatology 21: 561-569.] |

The importance of dietary selenium in the maintenance of human and animal health has been well established in the prior art.

The recognition of the essential role of selenium in human and animal nutrition has resulted in the establishment of a Recommended Daily Allowance (RDA) for humans and approval of the inclusion of additional selenium compounds in animal feed. Recently, the Food and Nutrition Board of the Institute of Medicine revised the RDA for selenium to 55 [mu] g [Dietary Reference Intakes for Vitamin C, Vitamin E, Selenium and Carotenoids. Washington, D.C.: National Academy Press, (2000)]. These inorganic selenium salts can be added at the level of 0.3 ppm Se in feed dry matter. In June 2000, the FDA approved the use of selenium yeast in poultry broiler and layer diets.

Several studies have demonstrated that selenium is more bioavailable from organic sources than from inorganic sources. Foremost among them are L-selenomethionine and L-Se-methylselenocysteine.

These synthetic seleno-amino acids pose certain challenges for cosmetic and topical uses such as (a) low water solubility; (b) crystals bearing water repellant properties; (c) low rate of dissolution; and (d) sometimes malodorous properties. To overcome these shortcomings, the present invention describes several short dipeptides incorporating separately L-selenomethionine and L-Se-methyl-selenocysteine, especially with L-glutamic acid, in particular the γ-L-glutamyl analogs.

The synthesis of γ-L-Glutamyl-Se-methyl-L-selenocysteine has been discussed by E. Block, M. Birringer, W. Jiang, T. Nakahoda, H. J. Thompson, P. J. Toscano, H. Uzar, X. Zhang, Z. Zhu in the J Agric. Food Chem., 49, 458 (2001). The method involves coupling the reactants triethylammonium-N-(trityl)-L-γ-glutamate and methyl ester hydrochloride of Se-methyl L-selenocysteine with dicyclohexylcarbodiimide. The resulting material is denuded of the protecting ester and triphenyl groups through the successive use of acid and alkali followed by an ion exchange column chromatographic purification. This method bears innate disadvantages like (a) being circuitous and involving complex steps like column purifications (b) not being adaptable to a large scale industrial manufacture (c) Unfavorable economics of a production method.

It is thus the principle object of the present invention to develop a novel synthetic method for the production of selenoproteins, wherein said method Will confer useful properties to the selenopeptide product that will help overcome inherent disadvantages associated with synthetic selenoacids; is simple to perform and adaptable to larger scale industrial manufacture; will consume less time to perform; and Will ensure a pure selenopeptide product that can be readily used without any need for further purification.

It is another object of the present invention to develop isomeric peptides of L-selenomethionine and Se-Methyl-L-selenocysteine through a novel synthetic process that would result in:

Stable, solid isomeric peptides of L-selenomethionine and Se-Methyl-L-selenocysteine; enhanced water solubility of the isomeric peptides of L-selenomethionine and Se-Methyl-L-selenocysteine; enhanced rate of dissolution of the isomeric peptides of L-selenomethionine and Se-Methyl-L-selenocysteine in water; enhanced bioavailability of the isomeric peptides of L-selenomethionine and Se-Methyl-L-selenocysteine; enhanced purity of the isomeric peptides of L-selenomethionine and Se-Methyl-L-selenocysteine which makes the peptides ready for use without any need for further purification; and isomeric peptides of L-selenomethionine and Se-Methyl-L-selenocysteine which are not malodorous and are suitable for cosmeceutical use.

It is another object of the present invention to evaluate isomeric peptides of L-selenomethionine and Se-Methyl-L-selenocysteine developed by a novel synthetic method for useful cosmeceutical properties such as vascular endothelial growth factor promoting activity and anti-5-alpha reductase activity.

It is another object of the present invention to develop cosmeceutical compositions comprising the isomeric peptides of L-selenomethionine and Se-Methyl-L-selenocysteine obtained by a novel synthetic method and which, are marked by (a) purity; (b) enhanced water solubility; (c) enhanced bioavailability; (d) excellent vascular endothelial growth factor promoting activity (e) excellent anti-5-alpha-reductase activity; and (f) the ability to stimulate "hair growth" and prevent/reduce "hair fall" thereby maintaining a perfect homeostasis for hair care.

It is another object of the present invention to develop pharmaceutical compositions comprising the isomeric peptides of L-selenomethionine and Se-Methyl-L-selenocysteine obtained by a novel synthetic method and which, are marked by (a) purity; (b) enhanced water solubility; (c) enhanced bioavailability; (d) excellent vascular endothelial growth factor promoting activity; (e) excellent anti-5-alpha-reductase activity; and (f) the ability to stimulate "hair growth" and prevent/reduce "hair fall" thereby maintaining a perfect homeostasis for hair care.

The present invention fulfills all these objectives and provides further related advantages.

SUMMARY OF THE INVENTION

The present invention discloses a novel synthetic method for obtaining isomeric peptides through the linkage of L-selenomethionine and Se-Methyl-L-selenocysteine with L-Glutamic acid in an appropriate manner. In one aspect of the present invention, the novel synthetic method involves linking L-selenomethionine and Se-Methyl-L-selenocysteine with L-glutamic acid separately in two distinct ways namely (i) the attachment of L-selenomethionine and Se-Methyl-L-selenocysteine through the γ-carboxylic acid group of L-Glutamic acid to form γ-L-Glutamyl-Se-methyl-L-selenocysteine (GGMSC) and γ-L-Glutamyl-L-selenomethionine(GGLSM) respectively; (ii) the attachment of L-selenomethionine and Se-Methyl-L-selenocysteine through the α-carboxylic acid group of L-Glutamic acid to form α-L-Glutamyl-Se-methyl-L-selenocysteine (AGMSC) and α-L-Glutamyl-L-selenomethionine (AGLSM) respectively. While the synthetic method proposed in this invention is discussed with reference to (i) γ-L-Glutamyl-Se-methyl-L-selenocysteine (GGMSC); (ii) γ-L-Glutamyl-L-selenomethionine (GGLSM); (iii) α-L-Glutamyl-Se-methyl-L-selenocysteine (AGMSC) and (iv) α-L-Glutamyl-L-selenomethionine (AGLSM) it is clearly evident that the novel synthetic route may also be adopted for the synthesis of all other isomeric peptides of L-selenomethionine and Se-Methyl-L-selenocysteine by an appropriate L-glutamic acid linkage.

The advantageous features of the present invention include,

A novel synthetic method for selenopeptides, wherein the said method will confer useful properties to the selenopeptide product that will help overcome inherent disadvantages associated with synthetic selenopeptides; is simple to perform and adaptable to larger scale industrial manufacture; will consume less time to perform; and will ensure a pure selenopeptide product that can be readily used without any need for further purification.

A novel synthetic method for the isomeric peptides through an appropriate linkage of L-selenomethionine and Se-Methyl-L-selenocysteine with L-glutamic acid that would result in stable, solid isomeric peptides of L-selenomethionine and Se-Methyl-L-selenocysteine; enhanced water solubility of the isomeric peptides of L-selenomethionine and Se-Methyl-L-selenocysteine; enhanced rate of dissolution of the isomeric peptides of L-selenomethionine and Se-Methyl-L-selenocysteine in water; enhanced bioavailability of the isomeric peptides of L-selenomethionine and Se-Methyl-L-selenocysteine; enhanced purity of the isomeric peptides of L-selenomethionine and Se-Methyl-L-selenocysteine which makes the proteins ready for use without any need for further purification; isomeric peptides of L-selenomethionine and Se-Methyl-L-selenocysteine which are not malodorous and are suitable for cosmeceutical use; isomeric peptides of L-selenomethionine and Se-Methyl-L-selenocysteine which are characterized by excellent vascular endothelial growth factor promoting activity and anti-5-alpha-reductase activity; isomeric peptides of L-selenomethionine and Se-Methyl-L-selenocysteine which will prevent/reduce "hair fall" and promote "hair growth" thereby maintaining a perfect homeostatic mechanism for hair care.

Isomeric peptides of L-selenomethionine and Se-Methyl-L-selenocysteine that have been obtained by the appropriate linkage of L-selenomethionine or Se-Methyl-L-selenocysteine with L-Glutamic acid which exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

Cosmeceutical compositions comprising the isomeric peptides obtained by a novel synthetic process involving an appropriate linkage of L-selenomethionine or Se-Methyl-L-selenocysteine with L-glutamic acid and, which exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

Pharmaceutical compositions comprising the isomeric peptides obtained by a novel synthetic process involving an appropriate linkage of L-selenomethionine or Se-Methyl-L-selenocysteine with L-glutamic acid and, which exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

Additionally, isomeric peptides obtained through the appropriate linkage of L-selenomethionine or Se-Methyl-L-selenocysteine with essential or non-essential amino acids, which exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

Additionally, cosmeceutical compositions that comprise isomeric peptides obtained through the appropriate linkage of L-selenomethionine or Se-Methyl-L-selenocysteine with essential or non-essential amino acids, which exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

Additionally, pharmaceutical compositions that comprise isomeric peptides obtained through the appropriate linkage of L-selenomethionine or Se-Methyl-L-selenocysteine with essential or non-essential amino acids, which exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

Other features and advantages of the present invention will become apparent from the following more detailed description, taken in conjunction with the accompanying figures, which illustrate, by way of example, the principle of the invention.

BRIEF DESCRIPTION OF FIGURES

FIG. 1a shows a schematic representation of selenoprotein biosynthesis in animals (prior art).

FIG. 1b shows the PMR of γ-(N-Phthaloyl-L-Glutamyl)-Se-methyl-L-selenocysteine.

FIG. 2 shows the Mass spectra of γ-L-glutamyl-Se-methyl-L-selenocysteine.

FIG. 3 shows the PMR of γ-L-glutamyl-Se-methyl-L-selenocysteine.

FIG. 4 shows the PMR of γ-L-Glutamyl-L-selenomethionine.

FIG. 5 shows the Single Crystal X-ray Structure of γ-L-Glutamyl-L-selenomethionine.

DETAILED DESCRIPTION OF THE PREFERRED EMBODIMENT

Figure 6:
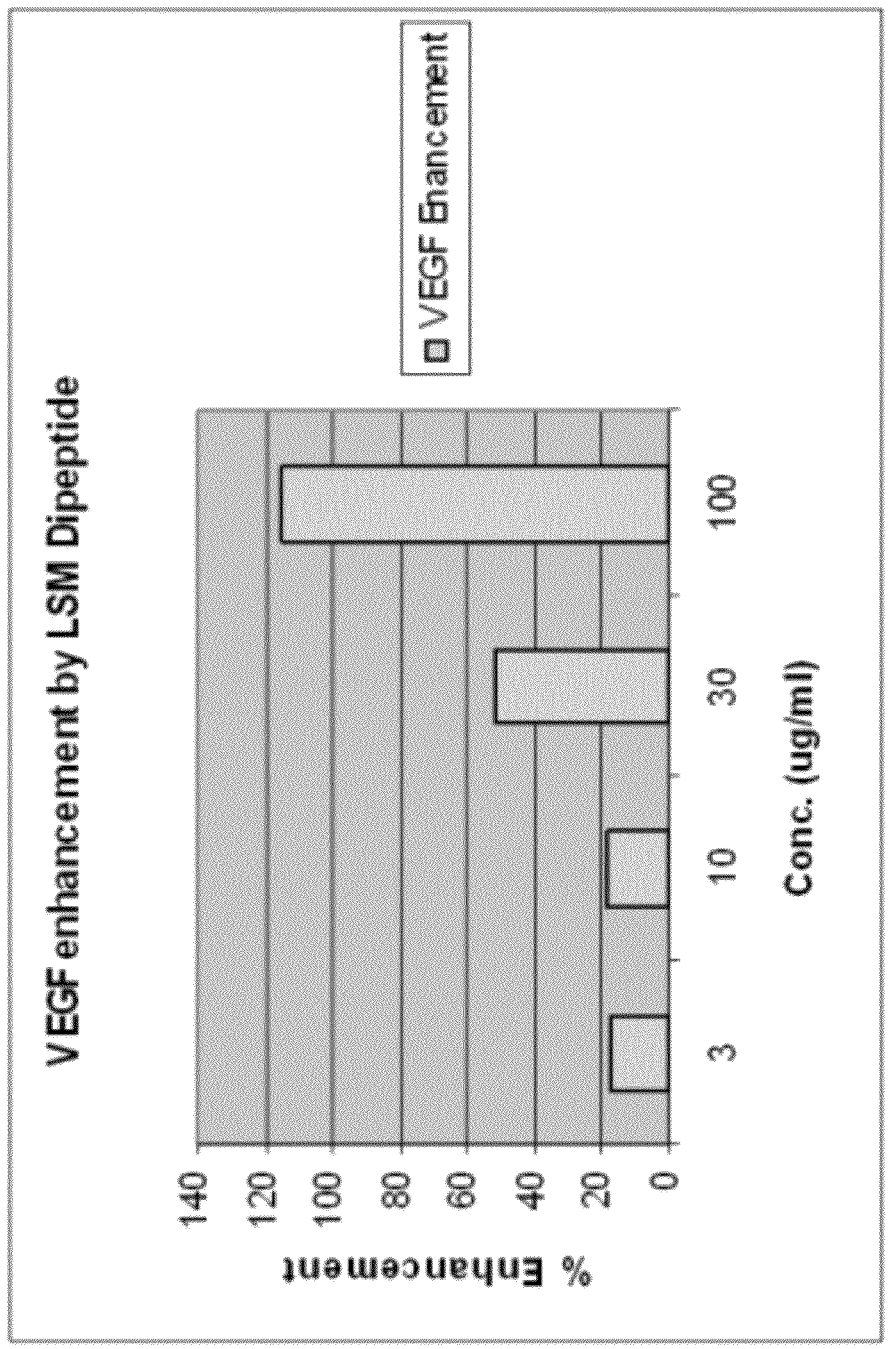
FIG. 6 shows a graphical representation of the effect of L-Selenomethionine dipeptides on vascular endothelial growth factor enhancement.
Figure 7:
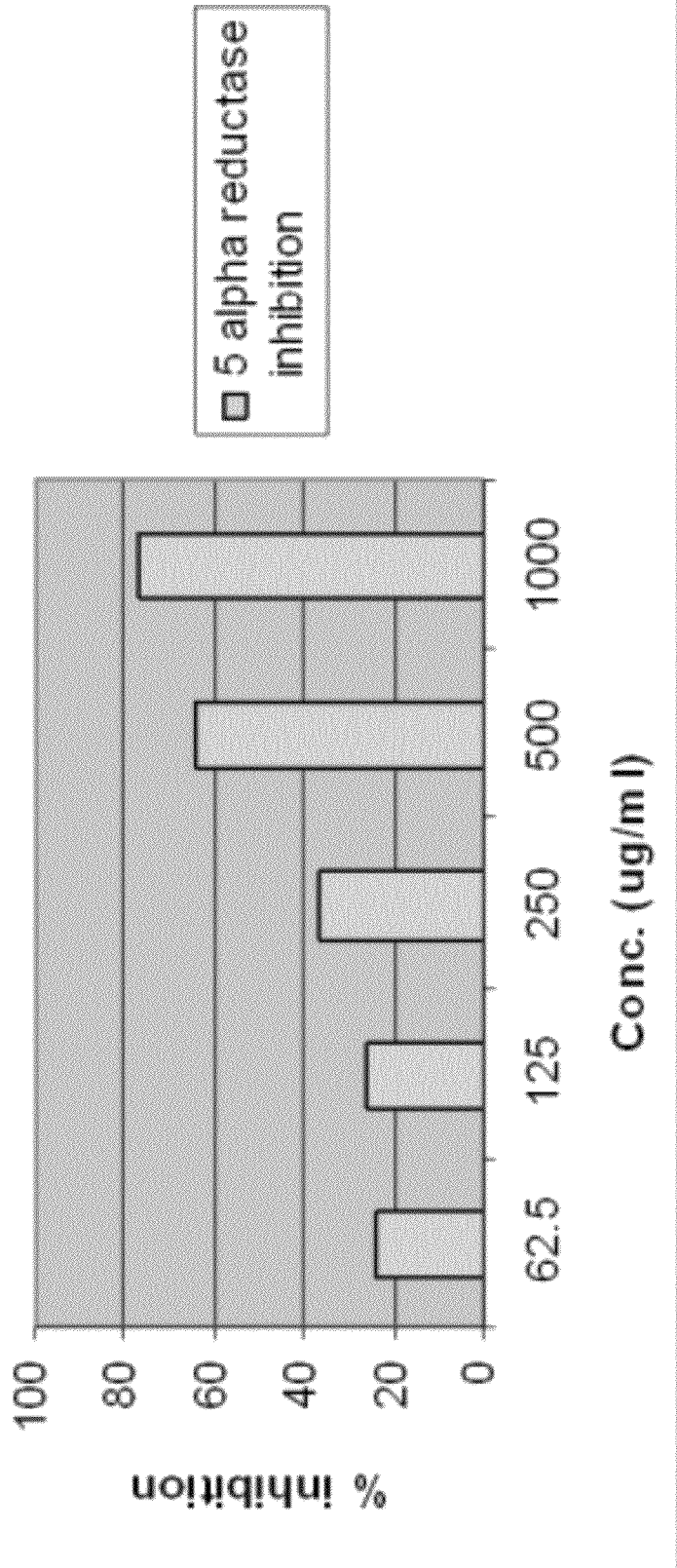
FIG. 7 shows a graphical representation of the inhibition of 5-alpha-reductase activity by L-Selenomethionine dipeptides.

Definitions (a) Cosmeceutical—The term "cosmeceutical" is now being universally used to define a cosmetic product claimed to have medicinal or drug-like or therapeutic benefits. Cosmeceutical products are marketed as cosmetics, but reputedly contain biologically active ingredients. [US20050191267, US20040241254, US20050079210, EP0858313, U.S. Pat. No. 6,149,896, US20060057075, US20060182770]. The term "cosmeceutical" as used in this application is to be construed to encompass the meaning set forth in the definition provided herein above.

In the most preferred embodiment, the present invention discloses a novel synthetic method for the isomeric peptides through an appropriate linkage of L-selenomethionine or Se-Methyl-L-selenocysteine with L-glutamic acid. In another preferred embodiment, the present invention discloses a novel synthetic method for isomeric peptides through an appropriate linkage of L-selenomethionine or Se-Methyl-L-selenocysteine with L-glutamic acid which results in stable, solid isomeric peptides of L-selenomethionine and Se-Methyl-L-selenocysteine; enhanced water solubility of the isomeric peptides of L-selenomethionine and Se-Methyl-L-selenocysteine; enhanced rate of dissolution of the isomeric peptides of L-selenomethionine and Se-Methyl-L-selenocysteine in water; enhanced bioavailability of the isomeric peptides of L-selenomethionine and Se-Methyl-L-selenocysteine; enhanced purity of the isomeric peptides of L-selenomethionine and Se-Methyl-L-selenocysteine which makes the proteins ready for use without any need for further purification; isomeric peptides of L-selenomethionine and Se-Methyl-L-selenocysteine which are not malodorous and are suitable for cosmeceutical use; isomeric peptides of L-selenomethionine and Se-Methyl-L-selenocysteine which exhibit excellent vascular endothelial growth factor stimulating properties and anti-5-alpha-reductase properties;

Isomeric peptides L-selenomethionine and Se-Methyl-L-selenocysteine which stimulate "hair growth" and prevent/reduce "hair fall" thereby maintaining a perfect homeostatic mechanism for hair care.

In yet another preferred embodiment, the present invention discloses a novel synthetic method for isomeric peptides through an appropriate linkage of L-selenomethionine or Se-Methyl-L-selenocysteine with L-glutamic acid, which is simple to perform; is adaptable to large scale industrial manufacture; consumes less time to perform; ensures a pure selenopeptide product that can be readily used without any need for further purification.

In yet another preferred embodiment, the present invention also discloses isomeric peptides obtained through the appropriate linkage of L-selenomethionine or Se-Methyl-L-selenocysteine with L-Glutamic acid, wherein the isomeric peptides; exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

In yet another preferred embodiment, the present invention discloses cosmeceutical compositions that comprise the isomeric peptides obtained through the appropriate linkage of L-selenomethionine or Se-Methyl-L-selenocysteine with L-glutamic acid, wherein the isomeric peptides exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

In yet another preferred embodiment, the present invention discloses pharmaceutical compositions that comprise the isomeric peptides obtained through the appropriate linkage of L-selenomethionine or Se-Methyl-L-selenocysteine with L-glutamic acid, wherein the isomeric peptides exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

In an additional embodiment, the present invention also includes isomeric peptides obtained through the appropriate linkage of L-selenomethionine or Se-Methyl-L-selenocysteine with essential or non-essential amino acids, wherein the isomeric peptides exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

In yet another additional embodiment, the present invention discloses cosmeceutical compositions that comprise the isomeric peptides obtained through the appropriate linkage of L-selenomethionine or Se-Methyl-L-selenocysteine with essential and non-essential amino acids, wherein the isomeric peptides exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the isomeric peptides are ready for use without the need for further purification; are not malodorous; are suitable for cosmeceutical use; and stimulate "hair growth" and prevent/reduce "hair fall" thereby maintaining a perfect homeostatic mechanism for hair care.

In yet another additional embodiment, the present invention discloses pharmaceutical compositions that comprise the isomeric peptides obtained through the appropriate linkage of L-selenomethionine or Se-Methyl-L-selenocysteine with essential and non-essential amino acids, wherein the isomeric peptides exhibit enhanced stability; exhibit enhanced water solubility; exhibit an enhanced rate of dissolution in water; exhibit enhanced bioavailability; exhibit excellent vascular endothelial growth factor stimulating activity; exhibit excellent anti-5-alpha-reductase activity; exhibit enhanced purity, whereby the said isomeric peptides are ready for use without the need for further purification; are not malodorous; are suitable for cosmeceutical use; and stimulate "hair growth" and prevent "hair fall" thereby maintaining a perfect homeostatic mechanism for hair care.

In a preferred embodiment, the essential amino acid is one selected from the group consisting of phenylalanine, leucine, methionine, lysine, isoleucine, valine, threonine, tryptophan, histidine and arginine.

In another preferred embodiment, the non-essential amino acid is one selected from the group consisting of alanine, arginine, aspartic acid, cysteine, cystine, glutamic acid, glutamine, glycine, ornithine, proline, serine, taurine, tyrosine, L-Se-methylselenocysteine, L-selenomethionine.

The novel synthetic method for isomeric peptides through an appropriate linkage of L-selenomethionine and Se-Methyl-L-selenocysteine with L-glutamic acid and the useful physical, chemical and biological properties of the said isomeric peptides are discussed herein below as specific examples in relevance to the isomeric peptides (i) γ-L-Glutamyl-Se-methyl-L-selenocysteine (GGMSC); (ii) γ-L-Glutamyl-L-selenomethionine (GGLSM); (iii) α-L-Glutamyl-Se-methyl-L-selenocysteine (AGMSC); and (iv) α-L-Glutamyl-L-selenomethionine (AGLSM). Further, general synthetic routes for making L-Selenomethionyl-Amino acid and Amino acid-L-selenomethionine dipeptide are also elucidated herein below.

EXAMPLE I

Synthesis of γ-(N-Phthaloyl-L-Glutamyl)-Se-methyl-L-selenocysteine

The sequence of reactions in the synthesis of γ-(N-Phthaloyl-L-Glutamyl)-Se-methyl-L-selenocysteine are represented as Steps 1-4 herein below. The reaction starts with the protection of amino group of L-glutamic acid as its phthaloyl derivative. While the phthaloyl protected derivative of L-glutamic acid had been prepared earlier using phthalic anhydride (H. Gu, Y. Jiang, Organic Prep. Proced. Int., 36(5), 479 (2004), they invariably result in complete or partial racemization and were difficult to adapt or reproduce. Another way of introducing phthaloyl groups onto the amino groups is the use of Nefken reagent (C. R. McArthur, P. M. Worster, A. U. Okon, Synthetic Communications 13, 311 (1983); C. R. McArthur, P. M. Worster, A. U. Okon, Synthetic Communications 13, 393 (1983)). However, the preparation and use of Nefken reagent have been reported to result in by-products (P. M. Worster, C. C. Leznoff, C. R. McArthur, J. Org. Chem., 45, 174 (1980).

The present invention uses (1-chloro-1,3-dihydro-3-oxo-1-isobenzofuranyl)-phosphonic acid diethyl ester for protection of amino groups of amino acids in aqueous medium alone. The preparation of (1-chloro-1,3-dihydro-3-oxo-1-isobenzofuranyl)-phosphonic acid diethyl ester from triethyl phosphite and phthaloyl chloride under neat conditions without the need for a solvent (step 1) is represented in Equation 1. Triethylphosphite is especially preferred in that it has no offensive odor associated with trimethylphosphite (J. Kehler & E. Breuer, Synthesis, 1419 (1998)).

EQUATION 1

Synthesis of (1-chloro-1,3-dihydro-3-oxo-1-isobenzofuranyl)-phosphonic acid diethyl ester

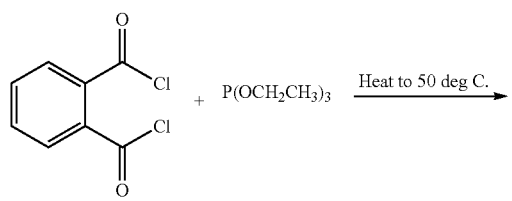

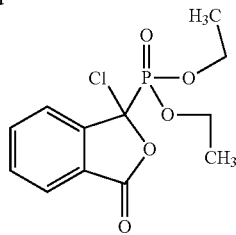

Step 1—The synthesis of (1-chloro-1,3-dihydro-3-oxo-1-isobenzofuranyl)-phosphonic acid diethyl ester is represented in Equation 1. Phthaloyl chloride (28.0 g, 138 mmol) was taken in a 250 ml RB flask equipped with a magnetic stirrer and dropping funnel. The solution was heated to about 50° C. and triethylphosphite (22.9 g, 138 mmol) was added slowly drop wise over a period of 0.5 hour. Stirring was continued for another 0.5 hour at this temperature. The reactants were stirred at room temperature for another 2 hours till the evolution of gases was ceased. The volatiles if any were removed under vacuum. The yield of (1-chloro-1,3-dihydro-3-oxo-1-isobenzofuranyl)-phosphonic acid diethyl ester was 41.7 g and the purity of the product as evaluated by Thin layer chromatography (TLC) was 99%. The product was ready to use without the need for further purification.

EQUATION 2

Synthesis of N-Phthaloyl-L-Glutamic Acid

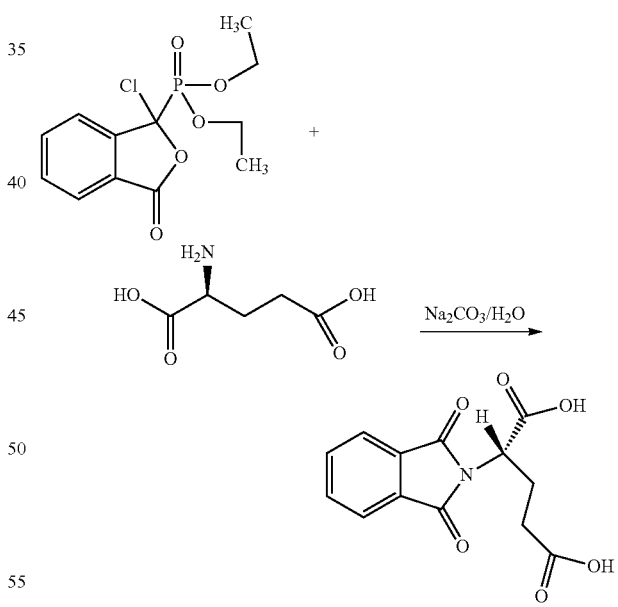

Step 2—The synthesis of N-Phthaloyl-L-Glutamic acid is represented in Equation 2. Sodium carbonate (36.5 g, 0.17 mol) in 170 ml of water was taken in a 500 ml RB flask equipped with a magnetic stirrer. L-Glutamic acid (25.0 g, 0.17 mol) was dissolved in the sodium carbonate solution. This solution was stirred at room temperature. After 15 minutes, (1-chloro-1,3-dihydro-3-oxo-1-isobenzofuranyl)-phosphonic acid diethyl ester (51.8 g, 0.17 mol) obtained from step 1, was added to this basic solution. After stirring for 5 hr at room temperature, the reaction mixture was filtered to remove any suspended particles. The pH of the solution was maintained at 1 to 2 with 6N HCl. The product N-phthaloyl-L-glutamic acid was then precipitated. The reaction mixture was further stirred for another 2 hr. The solid was filtered, washed with water and dried in vacuum. If needed, it could be crystallized from ethyl acetate/hexane; The yield of N-phthaloyl-L-glutamic acid was 32.6 g (70%); Melting point of N-phthaloyl-L-glutamic acid was found to be 159-161° C.; The specific rotation of N-phthaloyl-L-glutamic acid was −47.9 (c=3, dioxane). The purity of the product N-phthaloyl-L-glutamic acid was evaluated by TLC (Silica gel; Butan-1-ol: Water: Acetic acid 3:1:1)

EQUATION 3

Synthesis of N-Phthaloyl-L-Glutamic Anhydride

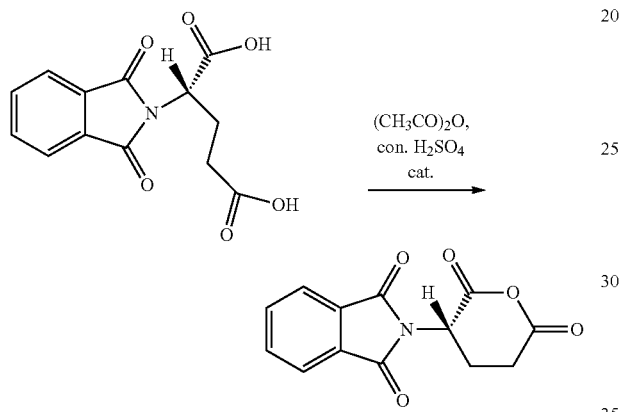

Step 3—The synthesis of N-Phthaloyl-L-glutamic anhydride is represented in Equation 3. N-phthaloyl-L-glutamic acid (10.0 g, 36.1 mmol) obtained in Step 2 in about 40 ml of acetic anhydride was taken in a 250 ml RB flask equipped with a magnetic stirrer and $CaCl_2$ drying guard tube. The solution was heated to 65° C. for about 15 min. A small quantity of concentrated sulfuric acid (300 μL) was added to obtain a clear solution within a short time. The reaction mixture was stirred for another 2 hrs at room temperature. The resultant white precipitate was cooled and filtered. The solid was washed with diethyl ether to remove traces of acetic acid/acetic anhydride. The yield of N-Phthaloyl-L-glutamic anhydride was 7.1 g (76%). The melting point of N-Phthaloyl-L-glutamic anhydride was 196-198° C. and the specific rotation of N-Phthaloyl-L-glutamic anhydride was −42° (c=3, dioxane).

EQUATION 4

Synthesis of γ-(N-Phthaloyl-L-Glutamyl)-Se-Methyl-L-Selenocysteine

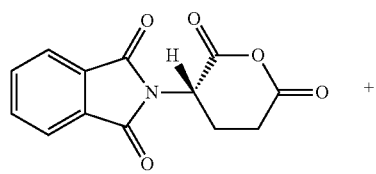

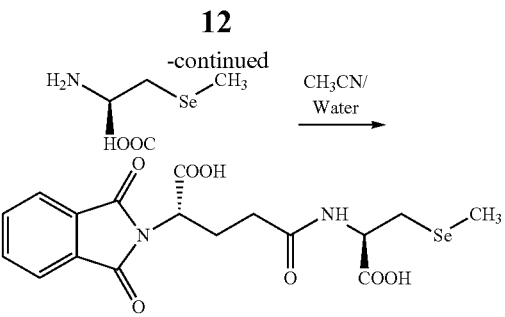

Step 4—The synthesis of γ-(N-Phthaloyl-L-Glutamyl)-Se-methyl-L-selenocysteine is represented in Equation 4. N-Phthaloyl-L-glutamic anhydride (7.5 g, 28.9 mmol), Se-Methyl-L-selenocysteine (5 g, 27.5 mmol) and acetonitrile (75 ml) were taken in a clean 250 ml RB flask. The mixture was stirred and heated to 65° C. Water (7.5 ml) was then added and the reaction mixture was kept at 65-70° C. for 5 hr. A clear solution was obtained. TLC of this clear solution (Butanol: water: acetic acid 6:2:2) showed near absence of starting materials. The reaction mixture was then cooled and any solid particles were removed by filtration. The filtrate was concentrated to get the product γ-(N-Phthaloyl-L-Glutamyl)-Se-methyl-L-selenocysteine weighing around 12-13 g. The Proton NMR structure of the product γ-(N-Phthaloyl-L-Glutamyl)-Se-methyl-L-selenocysteine is represented in FIG. 1b.

EQUATION 5

Hydrazinolysis of γ-L-Glutamyl-Se-Methyl-L-Selenocysteine

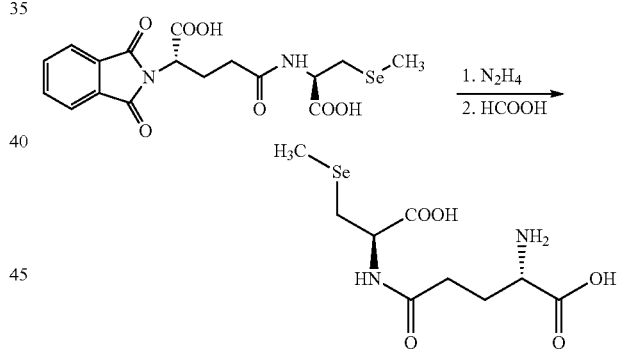

Step 5—The hydrazinolysis of γ-(N-Phthaloyl-L-Glutamyl)-Se-methyl-L-selenocysteine (12.5 g obtained from Step 4) is represented in Equation 5. γ-(N-Phthaloyl-L-Glutamyl)-Se-methyl-L-selenocysteine was dissolved in 125 ml methanol by heating in a 500 ml RB flask to obtain a clear solution. Hydrazine hydrate 55% (5 ml) was added to this clear solution under a temperature of 65-70° C. for 5-6 hrs. Completion of the reaction was evaluated by TLC. After completion of reaction, methanol was completely distilled out under vacuum. Water (75 ml) was added and the contents were stirred well for 1 hr. The dipeptide salt (the dipeptide forms a hydrazine salt during this reaction) dissolved completely leaving out the by-product residue, namely phthalhydrazide, as an insoluble residue. This by-product was removed by filtration and acetone (20 ml) was added to precipitate any further remaining by-products with the wanted dipeptide-hydrazine salt. Once again the by-product was removed by filtration. The filtrate was concentrated to dryness under vacuum at <60° C. The product was dissolved in water and again filtered. The filtrate was again concentrated to give the dipeptide as the hydrazine salt. Elemental analysis calculated for the hydrazine salt with molecular formula $C_9H_{20}N_4O_5Se$ C, 31.50; H: 5.87; N, 16.33; Se: 22.99. The values found were: C: 31.61; H, 5.64; N, 16.11; Se: 22.64. The dipeptide was liberated from hydrazine using formic acid. Thus the above hydrazine salt was dissolved in formic acid (95%) to get a clear solution. Then ethanol (100 ml) was added under constant stirring. The reaction was further stirred for 15 h at room temperature. The precipitated γ-L-glutamyl-Se-methyl-L-selenocysteine (GGMSC) was filtered and washed with ethanol. It was suck-dried under vacuum at 50-55° C. The yield of γ-L-glutamyl-Se-methyl-L-selenocysteine (GGMSC) was 5 g. The melting point of γ-L-glutamyl-Se-methyl-L-selenocysteine was 185-188° C. E. Block, M. Birringer, W. Jiang, T. Nakahoda, H. J. Thompson, P. J. Toscano, H. Uzar, X. Zhang, Z. Zhu in the J Agric. Food Chem., 49, 458 (2001) reports a mp of 159-161° C. with a low yield (12%) of the same product. The purity of the γ-L-glutamyl-Se-methyl-L-selenocysteine as evaluated by High Performance Liquid Chromatography (HPLC) was >99%. Elemental analysis values calculated for molecular formula C9H16N2O5Se C, 34.74 H, 5.18; N, 9.00; The values found were C, 34.81; H, 4.94; N, 9.06; The selenium analysis by Inductively Coupled Plasma (ICP) on samples of this material gave 25.0-25.4%. The specific optical rotation of γ-L-glutamyl-Se-methyl-L-selenocysteine was −12.2° (c=1, solvent water). Mass spectral and NMR spectroscopic data of γ-L-glutamyl-Se-methyl-L-selenocysteine (GGMSC) is represented in FIG. 2 and FIG. 3 respectively.

EXAMPLE II

Synthesis of γ-(N-Phthaloyl-L-Glutamyl)-L-Selenomethionine

The synthesis of γ-(N-phthaloyl-L-Glutamyl)-L-selenomethionine is outlined in (Equation 6; Step (i)) and (Equation 7; Step (ii)).

EQUATION 6

Synthesis of γ-(N-phthaloyl-L-Glutamyl)-L-selenomethionine from N-Phthaloyl-L-glutamic anhydride and L-selenomethionine

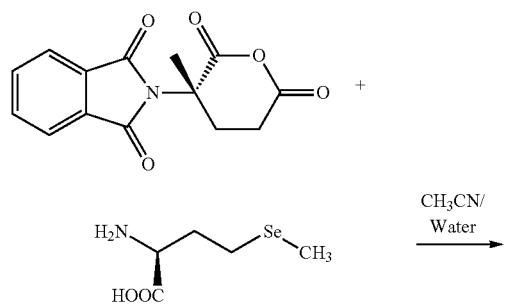

-continued

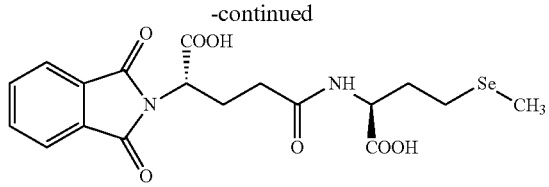

Step (i)—N-Phthaloyl-L-glutamic anhydride (13.25 g, 51.1 mmol) as obtained in Example I; Step 3 (represented by Equation 3), and L-selenomethionine (10 g, 51.0 mmol) were taken in a 500 ml RB flask containing acetonitrile (150 ml). The mixture was stirred with heating at 65° C. Water (30 ml) was added to the reaction mixture and the temperature was maintained at 65-70° C. for about 7-8 hrs. A clear solution was obtained. Completion of the reaction was evaluated by TLC. The reaction mixture was cooled and filtered to remove undissolved particles. The filtrate was concentrated to give the product, γ-(N-phthaloyl-L-Glutamyl)-L-selenomethionine weighing about 25 g.

EQUATION 7

Hydrazinolysis of γ-(N-phthaloyl-L-Glutamyl)-L-selenomethionine

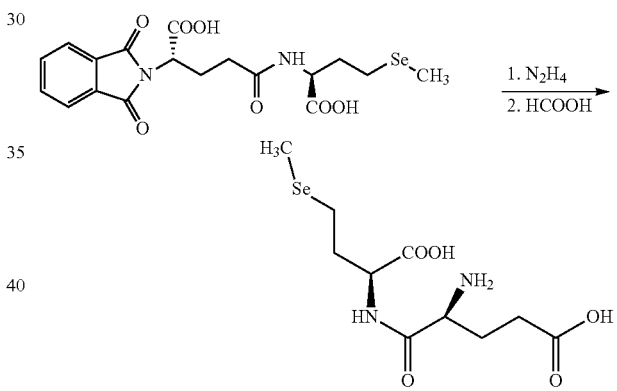

Step (ii)—γ-(N-phthaloyl-L-Glutamyl)-L-selenomethionine (25 g) obtained as represented in Equation 6 was dissolved in methanol (250 ml) by heating to 65° C. Hydrazine hydrate 55% (10 ml) was added to this solution and a temperature range of 65-70° C. was maintained for 10 hr. Completion of the reaction was evaluated by TLC. After the completion of the reaction, methanol was completely distilled out under vacuum. Water (150 ml) was added and the solution was stirred well for 1 hr at room temperature. The by-product of the reaction (phthalhydrazide) was insoluble and was filtered off. Acetone was added to the aqueous filtrate to precipitate further amounts of this by-product, phthalhydrazide. After removal of phthalhydrazide, the filtrate was concentrated to dryness under vacuum below <60° C. The residue obtained was dissolved in water (60 ml). This aqueous solution was filtered again to remove any undissolved particles. The filtrate was again concentrated to dryness. The residue thus obtained was treated with 95% formic acid (40 ml) to get a clear solution. Ethanol (200 ml) was added and the clear solution was stirred well for 15 hr at room temperature for complete precipitation. The product γ-L-Glutamyl-L-selenomethionine (GGLSM) was then filtered and dried under vacuum.

Further purification was done by crystallization from water. The yield of γ-L-Glutamyl-L-selenomethionine was 5 g. The product γ-L-Glutamyl-L-selenomethionine had a melting point of 192-194° C. The purity of γ-L-Glutamyl-L-selenomethionine (99%) was evaluated by HPLC analysis. Elemental analysis values calculated for molecular formula $C_{10}H_{18}N_2O_5Se$ are C, 36.93; H, 5.58; N, 8.61; The values found were C, 37.00; H, 5.49; N, 8.66; Selenium analysis on samples of this material by ICP method gave 23.8-24.2%. The Specific optical rotation of γ-L-Glutamyl-L-selenomethionine was −4.7° (c=1%, solvent water). Mass spectra were consistent with the structure showing the incorporation of one selenium per molecule as shown by the characteristic isotopic pattern of selenium. The proton (FIG. 4) and carbon NMR were also consistent with the structure. X-ray quality crystals of γ-L-Glutamyl-L-selenomethionine were grown and single crystal x-ray structure was obtained; The orthorhombic crystals belonged to the space group P212121 with unit cell lengths a=5.0583(2), b=9.6990(4), c=26.5142 (10); angles α=β=γ=90°; The three dimensional X-ray structure is represented in FIG. 5.

EXAMPLE III

Synthesis of α-Glutamyl-L-selenomethionine

The synthesis of α-Glutamyl-L-selenomethionine is outlined in (Equation 8; Step 1), (Equation 9; Step II), (Equation 10; Step III), (Equation 11; Step IV) and (Equation 12; Step V).

EQUATION 8

Synthesis of L-Selenomethionine methyl ester hydrochloride (LSM-OMe.HCl)

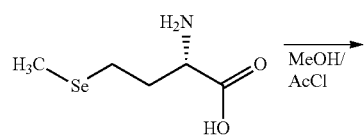

Step I—The synthesis of L-Selenomethionine methyl ester hydrochloride (LSM-OMe.HCl) is represented in Equation 8. L-Selenomethionine was added to a solution of acetyl chloride in methanol and the clear solution so obtained was stirred at room temperature till completion of the reaction (about 20 hrs). The solvents were removed in vacuum and the residue precipitated using dry diethyl ether.

EQUATION 9

Synthesis of N-t-Butoxycarbonyl-γ-t-butylglutamate [Boc-Glu (O-t-Bu)]

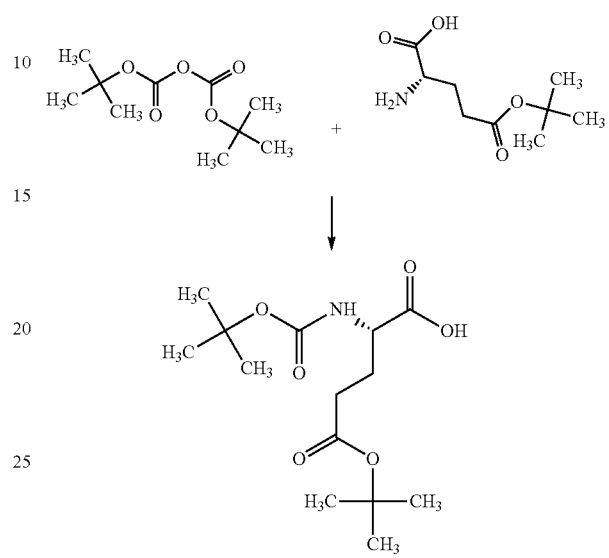

Step II—The synthesis of N-t-Butoxycarbonyl-γ-t-butylglutamate [Boc-Glu (O-t-Bu)] is represented in Equation 9. To a solution of Glu (O-t-Bu) in saturated sodium bicarbonate solution was added a solution of di-t-butyl pyrocarbonate in dioxane and the mixture was stirred at room temperature for about 20 hrs. Dioxane was removed from the reaction mixture. The aqueous solution was acidified with 10% $KHSO_4$ solution and the liberated Boc-Glu (O-t-Bu) was extracted into ethyl acetate. The ethyl acetate solution was washed with water, dried and concentrated. Precipitation was done using petroleum ether (60-800).

EQUATION 10

Synthesis of N-t-Butoxycarbonyl-γ-t-butyl-glutamyl-L-selenomethionine methyl ester [Boc-Glu (O-t-Bu)-LSM-OMe]

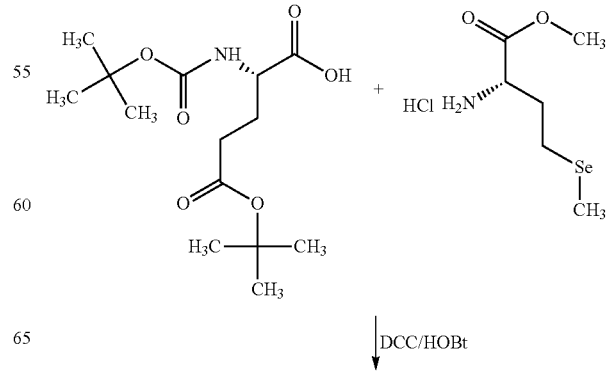

-continued

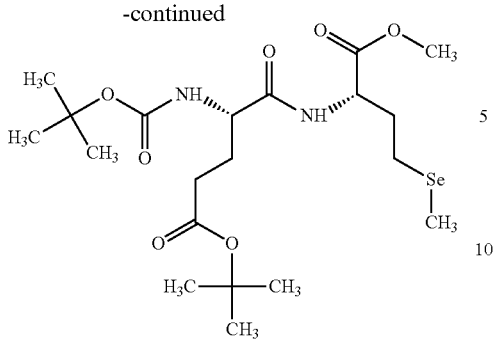

Step III—Synthesis of N-t-Butoxycarbonyl-γ-t-butyl-glutamyl-L-selenomethionine methyl ester [Boc-Glu (O-t-Bu)-LSM-OMe] is represented in Equation 10. To a solution of Boc-Glu (O-t-Bu) and HOBt in methylene chloride/DMF was added a solution of DCC in methylene chloride at 0° C. The mixture was stirred at low temperature for 30 min and at r.t. for 2 hrs. The insoluble DCU was filtered off. To the filtrate, a solution of HaLSM-0Me and triethylamine in methylene dichloride was added at low temperature. The mixture was stirred at r.t. overnight. It was then washed with 10% KHSO4, water, saturated NaHCO3 and water. Finally it was dried, concentrated and precipitated using petroleum ether (60-800).

EQUATION 11

Synthesis of N-t-Butoxycarbonyl-γ-t-butyl-glutamyl-L-selenomethionine [Boc-Glu (O-t-Bu)-LSM]

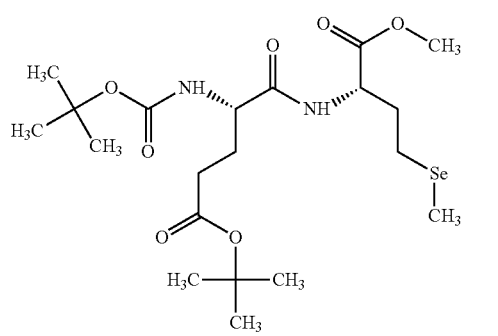

Step IV-Synthesis of N-t-Butoxycarbonyl-γ-t-butyl-glutamyl-L-selenomethionine [Boc-Glu (O-t-Bu)-LSM] is represented in Equation 11. Boc-Glu (O-t-Bu)-LSM-OMe was dissolved in MeOH. To the resulting solution, 2 M LiOH solution was added and stirred at room temperature for 2 hrs. The MeOH was then evaporated in vacuum. The aqueous layer was washed with ethyl acetate and acidified with 10% KHSO$_4$ solution. The liberated Boc-Glu (O-t-Bu)-LSM was extracted into ethyl acetate and washed with water. It was dried, concentrated and precipitated using petroleum ether (60-800). Mass spectra were in accordance with theory.

EQUATION 12

Synthesis of α-Glutamyl-L-selenomethionine (Glu-LSM)

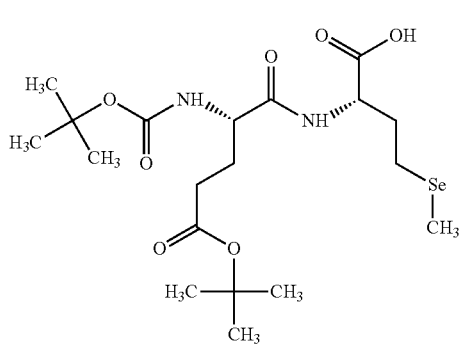

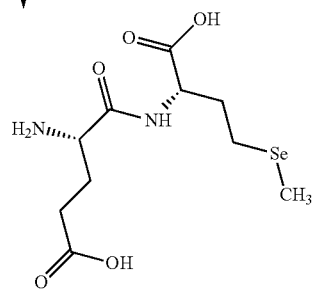

Step V-Synthesis of α-Glutamyl-L-selenomethionine (Glu-LSM) is represented in Equation 12. To a solution of Boc-Glu (O-t-Bu)-LSM in methylene dichloride, a solution of 10% TFA in methylene dichloride was added and the solution was stirred at 20° C. for about 60 min. The solvents were evaporated in vacuum and the residue was precipitated using methanol and dry diethyl ether. Desalting was done by passing an aqueous solution of the product through a weak anion exchanger resin. The melting point of the product was 168-170° C. Mass spectra with characteristic selenium isotopic pattern were obtained; Proton NMR (at 300 MHz, in D$_2$O solvent) was in accordance with the structure.

EXAMPLE IV

Synthesis of α-Glutamyl-L-Se-methylselenocysteine

Steps similar to the ones as discussed in Example III were followed for the synthesis of α-Glutamyl-L-Se-methylselenocysteine.

EXAMPLE V

Synthesis of L-Selenomethionyl-glutamic acid

Synthesis of L-Selenomethionyl-glutamic acid is discussed herein below in (Equation 13; Step A), (Equation 14; Step B), (Equation 15; Step C), (Equation 16; Step D) and (Equation 17; Step E).

EQUATION 13

Synthesis of N-t-Butyloxycarbonyl-L-selenomethionine (Boc-LSM)

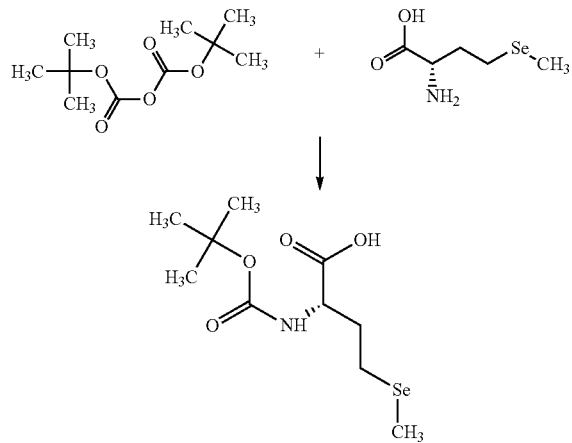

Step A-Synthesis of N-t-Butyloxycarbonyl-L-selenomethionine (Boc-LSM) is represented in Equation 13. To a solution of LSM in 2M NaOH was added a solution of di-t-butyl pyrocarbonate in dioxane and the mixture was stirred at room temperature for about 20 hrs. Dioxane was removed from the reaction mixture. The aqueous solution was acidified with 10% $KHSO_4$ solution and the liberated Boc-LSM was extracted into ethyl acetate. The ethyl acetate solution was washed with water, dried and concentrated. Precipitation was done using petroleum ether (60-800).

EQUATION 14

Synthesis of Dimethylglutamate hydrochloride (Glu(OMe)-OMe. HCl)

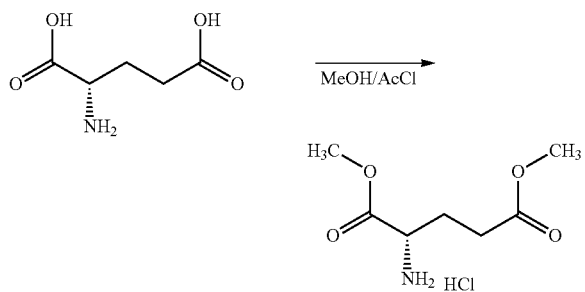

Step B-Synthesis of Dimethylglutamate hydrochloride (Glu (OMe)-OMe. HCl) is represented in Equation 14. Glutamic acid was added to a solution of AcCl in MeOH and the clear solution so obtained was stirred at room temperature till completion of the reaction (about 20 hrs). Solvents were removed in vacuum and the residue was precipitated using dry diethyl ether.

EQUATION 15

Synthesis of N-t-Butyloxycarbonyl-L-selenomethionyl-dimethyl glutamate (Boc-LSM-Glu (OMe)-OMe

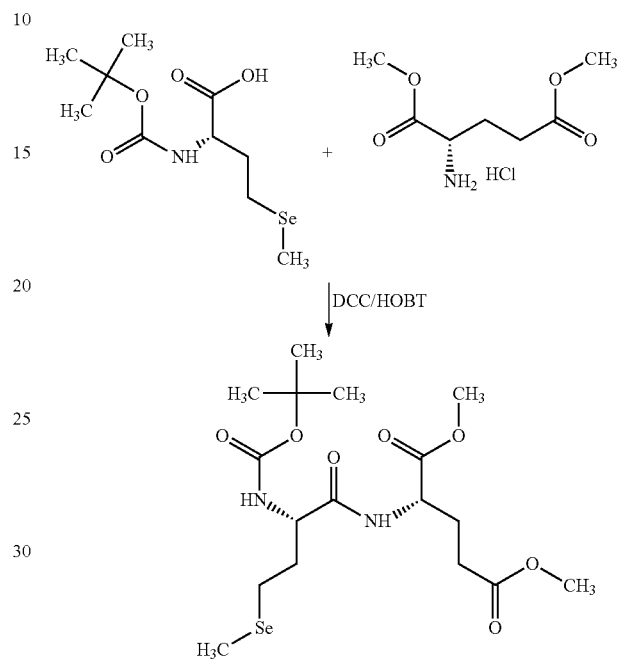

Step C-Synthesis of N-t-Butyloxycarbonyl-L-selenomethionyl-dimethyl glutamate (Boc-LSM-Glu (OMe)-OMe is represented in Equation 15. To a solution of Boc-LSM and HOBt in methylene chloride/DMF was added a solution of DCC in methylene chloride at 0° C. The mixture was stirred at low temperature for 30 min and at room temperature for 2 hrs. The insoluble DCU was filtered off. To the filtrate was added a solution of HCl.Glu (OMe)-OMe and triethylamine in methylene dichloride at low temperature. The mixture was stirred at room temperature overnight. It was then washed with 10% $KHSO_4$, water, saturated $NaHCO_3$ and water. Finally it was dried, concentrated and precipitated using petroleum ether (60-800). Mass spectrum was consistent with theory.

EQUATION 16

Synthesis of N-t-Butyloxycarbonyl-L-selenomethionyl-L-Glutamic acid (Boc-LSM-Glu)

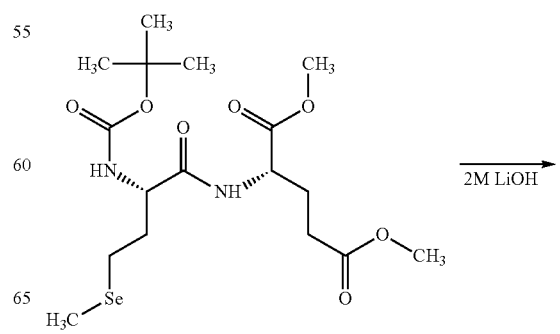

21

-continued

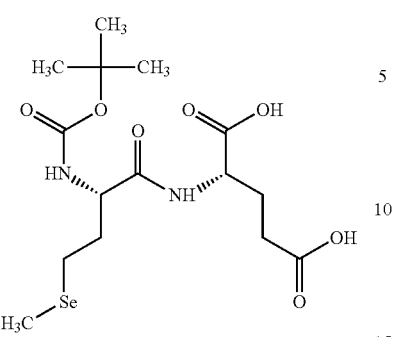

Step D-Synthesis of N-t-Butyloxycarbonyl-L-selenomethionyl-L-Glutamic acid (Boc-LSM-Glu) is represented in Equation 16. Boc-LSM-Glu (OMe)-OMe was dissolved in MeOH. To the resulting solution, 2M LiOH solution was added and stirred at room temperature for 2 hrs. The MeOH was then evaporated in vacuum. The aqueous layer was washed with ethyl acetate and acidified with 10% $KHSO_4$ solution. The liberated Boc-LSM-Glu was extracted into ethyl acetate and washed with water. It was dried, concentrated and precipitated using petroleum ether (60-800).

EQUATION 17

Synthesis of L-Selenomethionyl L-Glutamic acid (LSM-Glu)

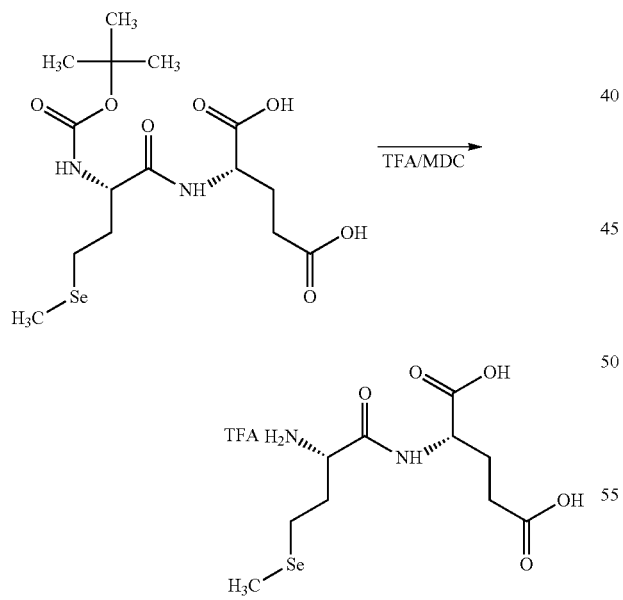

Step E-Synthesis of L-Selenomethionyl L-Glutamic acid (LSM-Glu) is represented in Equation 17. To a solution of Boc-LSM-Glu in methylene dichloride, a solution of 10% TFA in methylene dichloride was added and the mixture was stirred at 20° C. for about 60 min. The solvents were evaporated in vacuum and the residue was precipitated using methanol and dry diethyl ether. Desalting was done by passing an aqueous solution of the product through a weak anion exchanger resin. The melting point of L-Selenomethionyl L-Glutamic acid (LSM-Glu) was 148-150° C.; Mass spectra with correct molecular ions peak with characteristic selenium isotopic pattern was obtained. Proton NMR was in accord with structure.

EXAMPLE VI

Synthesis of L-Se-methyl-selenocysteinyl-glutamic acid

L-Se-methyl-selenocysteinyl-glutamic acid was made by a similar sequence of steps described in Example V.

EXAMPLE VII

Synthesis of L-Tyrosinyl-L-selenomethionine

The synthesis of L-Tyrosinyl-L-selenomethionine is discussed herein below as (Equation 18; Step (a)), (Equation 19; Step (b)), (Equation 20; Step (c)), (Equation 21; Step (d)) and (Equation 22; Step (e)).

EQUATION 18

Synthesis of N-Butyloxycarbonyl-Tyrosine (Boc-Tyr)

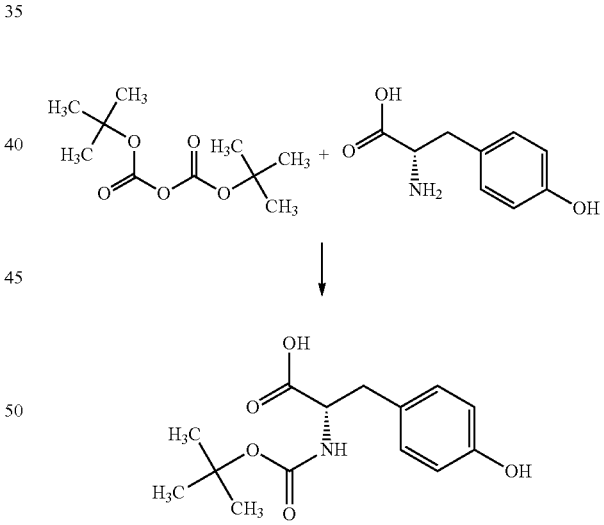

Step (a)—Synthesis of N-Butyloxycarbonyl-Tyrosine (Boc-Tyr) is represented in Equation 18. To a solution of Tyrosine in 2M NaOH was added a solution of di-t-butyl pyrocarbonate in dioxane and the mixture was stirred at room temperature for about 20 hrs. Dioxane was removed from the reaction mixture. The aqueous solution was acidified with 10% $KHSO_4$ solution and the liberated Boc-Tyr was extracted into ethyl acetate. The ethyl acetate solution was washed with water, dried and concentrated. Precipitation was done using petroleum ether (60-800).

EQUATION 19

L-Selenomethionine methyl ester Hydrochloride (LSM-OMe.HCl)

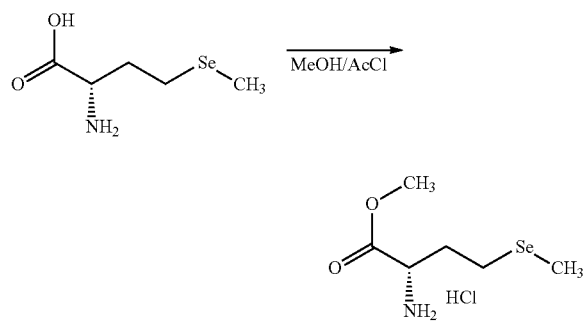

Step (b)—Synthesis of L-Selenomethionine methyl ester Hydrochloride (LSM-OMe.HCl) is represented in Equation 19. L-Selenomethionine was added to a solution of AcCl in MeOH and the clear solution so obtained was stirred at room temperature till completion of the reaction (about 20 hrs). Solvents were removed in vacuum and the residue was precipitated using dry diethyl ether.

EQUATION 20

Synthesis of N-Butyloxycarbonyl-Tyrosinyl-L-Selenomethionine methyl ester (Boc-Tyr-LSM-OMe)

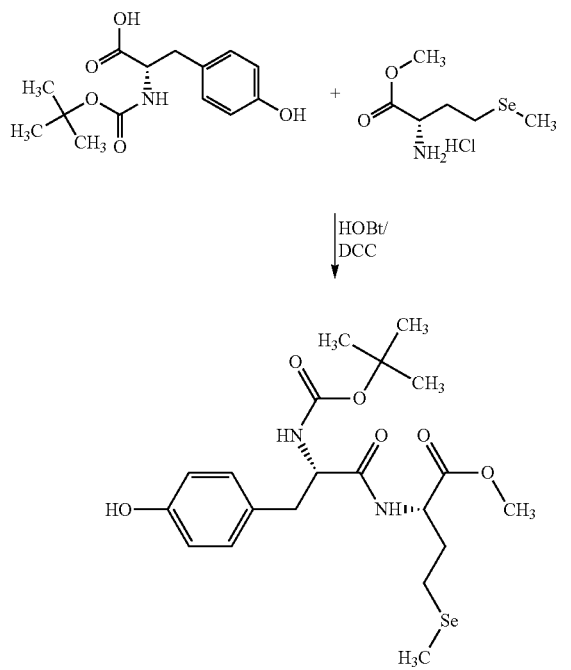

Step (c)—Synthesis of N-Butyloxycarbonyl-Tyrosinyl-L-Selenomethionine methyl ester (Boc-Tyr-LSM-OMe) is represented in Equation 20. To a solution of Boc-Tyr and HOBt in methylene chloride/DMF was added a solution of DCC in methylene chloride at 0° C. The mixture was stirred at low temperature for 30 min and at r.t. for 2 hrs. The insoluble DCU was filtered off. To the filtrate, a solution of HaLSM-OMe and triethylamine in methylene dichloride was added at low temperature. The mixture was stirred at room temperature overnight. It was then washed with 10% $KHSO_4$, water, saturated $NaHCO_3$ and water. Finally it was dried, concentrated and precipitated using petroleum ether (60-800).

EQUATION 21

Synthesis of N-Butyloxycarbonyl-Tyrosinyl-L-Selenomethionine (Boc-Tyr-LSM)

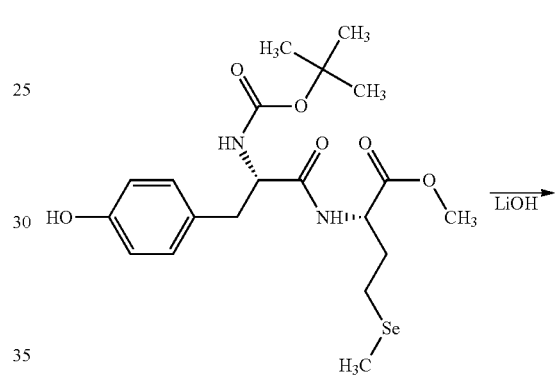

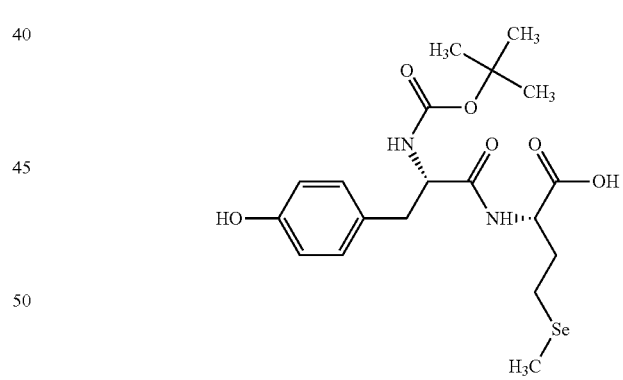

Step (d)—Synthesis of N-Butyloxycarbonyl-Tyrosinyl-L-Selenomethionine (Boc-Tyr-LSM) is represented in Equation 21. Boc-Tyr-LSM-OMe was dissolved in MeOH. To the resulting solution, 2 M LiOH solution was added and stirred at room temperature for 2 hrs. The MeOH was then evaporated in vacuum. The aqueous layer was washed with ethyl acetate and acidified with 10% $KHSO_4$ solution. The liberated Boc-Tyr-LSM was extracted into ethyl acetate and washed with water. It was dried, concentrated and precipitated using petroleum ether (60-800).

EQUATION 22

Synthesis of Tyrosinyl L-Selenomethionine (Tyr-LSM)

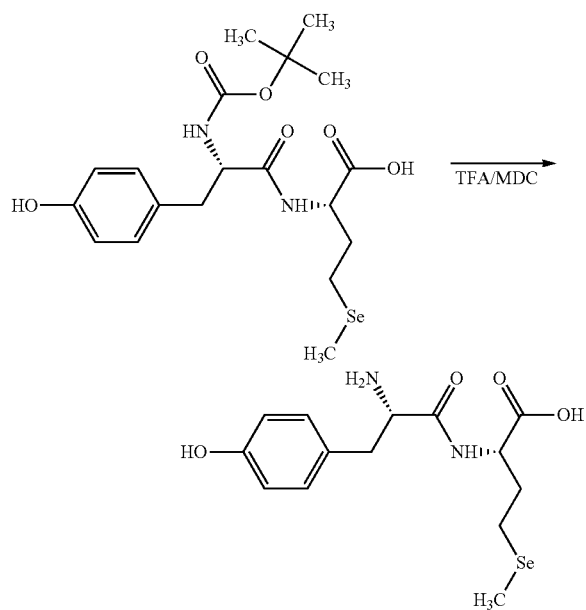

Step (e)—The synthesis of Tyrosinyl L-Selenomethionine (Tyr-LSM) is represented in Equation 22. To a solution of Boc-Tyr-LSM in methylene dichloride, a solution of 10% TFA in methylene dichloride was added and the solution was stirred at 20° C. for about 60 min. The solvents were evaporated in vacuum and the residue was precipitated using methanol and dry diethyl ether. Desalting was done by passing an aqueous solution of the product through a weak anion exchanger resin. Mass spectra with correct molecular ion peaks for different selenium isotopes in the expected ratios were obtained.

General procedures for making L-Selenomethionyl-Amino acid (The amino acids are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine)

t-butyloxycarbonyl-LSM (Boc-LSM) is coupled with suitably protected (side chain whenever applicable) amino acid methyl ester hydrochlorides by active ester method employing Hydroxybenzotriazole and Dicylcohexylcarbodiimide (HOBt and DCC). The unreacted Boc-LSM and HOBt are removed by washing the reaction mixture with saturated bicarbonate solution. The unreacted amino acid methyl ester is removed from the reaction mixture by washing it with 10% bisulphate solution. Boc-LSM-amino acid methyl esters are isolated by precipitation using ethyl acetate-petroleum ether (60-800). Boc-LSM-amino acid methyl esters are then converted to LSM-amino acids by carrying out saponification using 2M LiOH to liberate C-terminal carboxylic group, treatment with suitable reagent to remove any protecting group on the side chain of amino acid and acidolysis with Trifluoroacetic acid and Methylenedichloride (TFA/MDC) to liberate N-terminal amino group. The dipeptides are isolated by precipitation using methanol and diethyl ether. Desalting is done by treating an aqueous solution of the peptide with weak anion exchanger resin.

General procedures for making Amino acid-L-selenomethionine dipeptide (The amino acid refers to alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine (See example VII) and valine)

Side-chain protected Boc-amino acid is coupled with LSM methyl ester hydrochloride by active ester method employing HOBt and DCC. The unreacted Boc-amino acid and HOBt are removed by washing the reaction mixture with saturated bicarbonate solution. The LSM methyl ester is removed from the reaction mixture by washing it with 10% bisulphate solution. Boc-amino acid-LSM methyl esters are isolated by precipitation using ethyl acetate-petroleum ether (60-800).

Boc-amino acid-LSM methyl esters are then converted to amino acids-LSM by carrying out saponification using 2M LiOH to liberate C-terminal carboxylic group, treatment with suitable reagent to remove any protecting group on the side chain of amino acid and acidolysis with TFA/MDC to liberate N-terminal amino group. The dipeptides are isolated by precipitation using methanol and diethyl ether. Desalting is done by treating an aqueous solution of the peptide with weak anion exchanger resin.

EXAMPLE VIII

Biological activity of L-selenomethionine dipeptides

Vascular Endothelial Growth Factor (VEGF) Enhancement by L-Selenomethionine Dipeptides HaCaT Keratinocyte cells are challenged with $H_2O_2$ after treatment with the test samples. After 12 hr of activation with $H_2O_2$, the medium is collected for VEGF estimation by ELISA. The percentage enhancement of VEGF by varying concentrations of L-selenomethionine dipeptides of the present invention is illustrated in Table I.

TABLE I

| Concentration of L-selenomethionine dipeptides | Percentage VEGF enhancement |
|---|---|
| 0.3 (0.923 µM) | Nil |
| 3 (9.23 µM) | 17 |
| 10 (30.77 µM) | 18 |
| 30 (92.3 µM) | 52 |
| 100 (307.7 µM) | 115 |

Anti-5-Alpha-Reductase Activity

Activity of 5-Alpha-reductase enzyme (from rat liver microsomes) on substrate testosterone (40 µM) was assayed in presence of cofactor NADPH (56 µM) and LSM dipeptide over a time interval of 15 minutes. The absorbance was measured at 340 nm. (Table II)

TABLE II

| Concentration of LSM-dipeptide (ug/ml) | % inhibition of 5-alpha reductase |
|---|---|
| 62.5 | 24 |
| 125 | 26 |
| 250 | 37 |
| 500 | 64 |
| 1000 | 77 |

EXAMPLE IX

Aqueous Solubility Measurements

Aqueous solubility measurements were done on L-Se-methylselenocysteine and γ-L-glutamyl-L-Se-methylselenocysteine; The solubility of L-Se-methylselenocysteine was ca. 10% with dissolution occurring in two hours in water. The solubility of γ-L-glutamyl-L-Se-methylselenocysteine was ca. 25% with dissolution occurring in thirty minutes in water.

While the invention has been described with reference to a preferred embodiment, it is to be clearly understood by those skilled in the art that the invention is not limited thereto. Rather, the scope of the invention is to be interpreted only in conjunction with the appended claims.

The invention claimed is:

1. A method of preparing γ-L-glutamyl-L-Selenomethionine comprising steps of:
  a) reacting glutamic acid with P-(1-chloro-1,3-dihydro-3-oxo-1-isobenzofuranyl)-phosphonic acid diethyl ester in aqueous sodium carbonate or potassium carbonate solution to form N-phthaloyl-L-glutamic acid;
  b) reacting N-phthaloyl-L-glutamic acid with acetic anhydride to produce N-phthaloyl-L-glutamic anhydride;
  c) reacting N-phthaloyl-L-glutamic anhydride with L-selenomethionine to produce γ-(N-phthaloyl-L-glutamyl)-L-selenomethionine; and
  d) deprotecting the product of step (c) by hydrazinolysis of the phthalimide group to yield γ-L-glutamyl-L-selenomethionine.

2. A method of increasing production of VEGF (vascular endothelial growth factor) comprising step of contacting keratinocytes or scalp of a human subject in need thereof with γ-L-glutamyl-L-selenomethionine.

3. A method of inhibiting 5-alpha reductase comprising step of administering the compound γ-L-glutamyl-L-selenomethionine to a subject in need thereof.

* * * * *